United States Patent [19]

Sircar et al.

[11] Patent Number: 4,806,642
[45] Date of Patent: Feb. 21, 1989

[54] PURINE DERIVATIVES

[75] Inventors: Jagadish C. Sircar, Ann Arbor, Mich.; Charles F. Schwender, Gladstone, N.J.; Mark J. Suto, Ann Arbor, Mich.

[73] Assignee: Warner-Lambert Company, Morris Plains, N.J.

[21] Appl. No.: 22,467

[22] Filed: Mar. 6, 1987

Related U.S. Application Data

[63] Continuation of Ser. No. 657,211, Oct. 5, 1984, abandoned, which is a continuation-in-part of Ser. No. 547,297, Oct. 31, 1983, abandoned.

[51] Int. Cl.$^4$ ............... C07D 473/18; C07D 473/24; C07D 473/30; C07D 473/38
[52] U.S. Cl. .................................. 544/244; 544/265; 544/276
[58] Field of Search ............ 544/244, 265, 276; 514/81, 262

[56] References Cited

U.S. PATENT DOCUMENTS

| | | | |
|---|---|---|---|
| 4,199,574 | 4/1980 | Schaeffer | 544/244 X |
| 4,347,360 | 8/1982 | Ogilvie | 544/276 |
| 4,355,032 | 10/1982 | Verheyden et al. | 514/262 |
| 4,360,522 | 11/1982 | Schaeffer | 544/244 X |
| 4,579,849 | 3/1986 | MacCoss et al. | 514/262 |
| 4,714,701 | 12/1987 | Beauchamp | 514/258 |

FOREIGN PATENT DOCUMENTS 161955 11/1985 European Pat. Off.
864003348 2/1986 European Pat. Off.

OTHER PUBLICATIONS

Borel, et al., Immunology, vol. 32 (1977) 1017.
Ikehara, et al., Chem. Abstracts, vol. 66, (1967), entry 85984.
Fanci, ed., Human B-Lymphocyte Function, Raven Press N.Y., (1982) p. 73 article by Saxon, et al.
Shewach, et al., Cancer Research, vol. 46 (Feb. 1983) pp. 519-523.
Merck Manual 14th ed. (1982) pp. 328-331.
LeGrue, et al., Chem. Abstracts vol. 106:27545a (1986).
Kazmers, et al, Science, vol. 214, Dec. 81, pp. 1137-1139.
Kentaro Anzai, et al, Bulletin of the Chemical Society of Japan, vol. 47(2), (1974) pp. 417-420.
Burger, ed., Medicinal Chemistry, 2nd ed., Interscience Pub. (1960), p. 42.
Merck Index, 10th edition, p. 146.
"Inhibition of Human Purine Nucleoside . . .", Biochemical Pharmacology, vol. 36, No. 8, pp. 1237-1244, 1987, Stein.
Chemical Abstracts, vol. 66; 85984j, p. 8064.
Abstract from Pharmaceuticals, p. 4, week 8545—Derwent 85-263355/43=DE 3521-303-A.

Primary Examiner—Donald G. Daus
Assistant Examiner—Diana G. Rivers
Attorney, Agent, or Firm—Joan Thierstein

[57] ABSTRACT

Novel purine derivatives are described as agents for treating autoimmune diseases as well as a method of manufacture and pharmaceutical compositions as well as novel intermediates in the manufacture thereof.

13 Claims, No Drawings

PURINE DERIVATIVES

This is a continuation of U.S. application Ser. No. 657,211 filed Oct. 5, 1984 now abandoned which is a continuation-in-part of U.S. application Ser. No. 547,297 filed Oct. 31, 1983, now abandoned.

SUMMARY OF THE INVENTION

The present invention relates to a compound of the formula

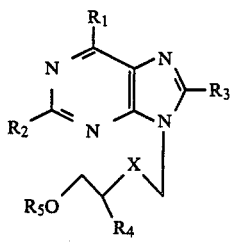

1 wherein $R_1$ is OH or SH; $R_2$ is hydrogen, NHR in which R is hydrogen or $COR_6$ where $R_6$ is alkyl of 1–4 carbon atoms, aryl or arylalkyl; $R_3$ is bromine or NHR where R is hydrogen or $COR_6$; X is O or S; $R_4$ is hydrogen or $CH_2OR_5$ in which $R_5$ is hydrogen, alkyl of 1–8 carbon atoms, aryl arylalkyl,

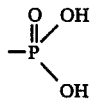

or $COR_6$, or a pharmaceutically acceptable acid or base addition salt thereof.

In a second generic aspect, the present invention relates to a compound of the formula 1 wherein $R_1$ is OH or SH; $R_2$ is hydrogen or NHR in which R is hydrogen or $COR_6$ where $R_6$ is alkyl of one to four carbon atoms, aryl or arylalkyl; $R_3$ is hydrogen; X is O or S; $R_4$ is alkyl of one to eight carbon atoms, aryl or arylalkyl, and $R_5$ is hydrogen, or a pharmaceutically acceptable acid or base addition salt therof.

In a third generic aspect, the present invention relates to a compound of the formula 1 wherein $R_1$ is OH or SH; $R_2$ is hydrogen or NHR in which R is hydrogen or $COR_6$ where $R_6$ is alkyl of one to four carbon atoms, aryl or arylalkyl; $R_3$ is hydrogen; X is O or S; $R_4$ is $CH_2OR_7$ in which $R_7$ is alkyl of one to eight carbon atoms, cycloalkyl of five to seven ring members, cycloalkylalkyl, aryl or arylalkyl, and $R_5$ is hydrogen, or a pharmaceutically acceptable acid or base addition salt thereof.

The present invention includes a method of manufacture, pharmaceutical composition comprising an effective amount of a compound of the formula 1 in all three generic aspects with a pharmaceutically acceptable carrier, as well as a method of treatment of autoimmune diseases such as arthritis, systemic lupus erythematosus, inflammatory bowel diseases, transplantation, juvenile diabetes, myasthenia gravis, multiple sclerosis as well as viral infections and cancer by administering an effective amount of a compound of the formula 1 in all three generic aspects in unit dosage form.

DETAILED DESCRIPTION

The term "alkyl of 1–8 carbon atoms" means a straight or branched hydrocarbon chain up to 8 carbon atoms such as, for example, methyl, ethyl, propyl, isopropyl, butyl, isobutyl, sec-butyl, tertiary-butyl, or octyl.

The term "cycloalkyl of five to seven ring members" means cyclopentyl, cyclohexyl, or cycloheptyl.

The term "cycloalkylalkyl" means a cyclopentyl, cyclohexyl, or cycloheptyl radical attached to an alkyl chain of up to four carbon atoms, straight or branched, such as for example, cyclohexylmethyl or cyclohexylethyl.

The term "aryl" includes unsubstituted and substituted aromatic ring such as, phenyl or phenyl substituted by halo, e.g., fluoro, chloro, bromo, or alkyl of 1–4 carbon atoms, such as methyl or ethyl, hydroxy, alkoxy of 1–4 carbon atoms, such as methoxy or ethoxy, or trifluoromethyl.

The term "arylalkyl" means an aromatic ring attached to an alkyl chain of up to 4 carbon atoms, such as unsubstituted or substituted phenylethyl or benzyl where the substituents on the aromatic ring may be the same as defined above.

Pharmaceutically acceptable base salts of the phosphate ester, where $R_5$ is

are the alkali metals, ammonium or substituted ammonium salts, such as sodium, potassium, and ammonium salts. The base salts may be prepared by standard methods known in the art.

Pharmaceutically acceptable acid addition salts are those derived from inorganic acids such as hydrochloric, sulfuric and the like, as well as organic acids such as methanesulfonic, toluenesulfonic, tartaric acid, and the like. These salts may also be prepared by standard methods known in the art.

Other pharmaceutically acceptable salts are those derived from inorganic bases such as sodium hydroxide, potassium hydroxide or ammonium hydroxide or organic bases such as arginine, N-methyl glucamine, and the like. These salts may also be prepared by standard methods known in the art.

A preferred embodiment of the present invention in its first generic aspect is a compound of formula 1 wherein $R_1$ is OH or SH; $R_2$ is hydrogen or NHR in which R is hydrogen or $COR_6$ where $R_6$ is alkyl of 1–4 carbon atoms or phenyl; $R_3$ is bromine or $NH_2$; X is O or S; $R_4$ is hydrogen or $CH_2OR_5$ in which $R_5$ is hydrogen, alkyl of 1–8 carbon atoms, benzyl or phenyl, or a pharmaceutically acceptable acid addition or base salt.

Another preferred embodiment of the present invention in its first generic aspect is a compound of formula 1 wherein $R_1$ is OH; $R_2$ is hydrogen or $NH_2$; $R_3$ is bromine or $NH_2$; X is O; $R_4$ is hydrogen or $CH_2OR_5$ in which $R_5$ is hydrogen or a pharmaceutically acceptable acid addition or base salt.

Particular embodiments of the present invention in its first generic aspect include 2,8-diamino-9-[(2-hydroxyethoxy)methyl]-9H-purin-6-ol, 2-[(2,8-diamino-6-hydroxy-9H-pyrin-9-yl)methoxy]-1,3-propanediol, 2,8- diamino-1,9-dihydro-9-[[1-(hydroxymethyl)-2-phenoxyethoxy)methyl]-6H-purin-6-one and 2-[(2-amino-8-bromo-6-hydroxy-9H-purin-9-yl)methoxy]-1,3-propanediol. The latter compound is not only useful pharmacologically but is also useful as an intermediate for preparing certain compounds of the present invention.

A preferred embodiment of the present invention in its second generic aspect is a compound of formula 1, wherein $R_1$ is OH; $R_2$ is hydrogen or NHR in which R is hydrogen or $COR_6$ where $R_6$ is alkyl of one to four carbon atoms, phenyl or benzyl; $R_3$ is hydrogen; X is O; $R_4$ is alkyl of one to eight carbon atoms, phenyl or benzyl, and $R_5$ is hydrogen, or a pharmaceutically acceptable acid addition or base salt.

Another preferred embodiment of the present invention in its second generic aspect is a compound of formula 1, wherein $R_1$ is OH; $R_2$ is hydrogen or NHR in which R is hydrogen or $COR_6$ where $R_6$ is methyl; $R_3$ is hydrogen; X is O; $R_4$ is alkyl of four to eight carbon atoms, phenyl or benzyl, and $R_5$ is hydrogen or a pharmaceutically acceptable acid addition or base salt.

Particular embodiments of the present invention in its second generic aspect include 2-amino-1,9-dihydro-9-[[[1-(hydroxymethyl)hexyl]oxy]methyl]-6H-purin-6-one and 2-amino-1,9-dihydro-9[[[1-(hydroxymethyl)-nonyl]oxy]methyl]-6H-purin-6-one. The above compounds are not only useful pharmacologically but are also useful as intermediates for preparing certain compounds of formula 1 of the present invention in its first generic aspect.

A preferred embodiment of the present invention in its third generic aspect is a compound of formula 1, wherein $R_1$ is OH; $R_2$ is hydrogen or NHR in which R is hydrogen or $COR_6$ where $R_6$ is alkyl of one to four carbon atoms, phenyl or benzyl; $R_3$ is hydrogen; X is O; $R_4$ is $CH_2OR_7$ in which $R_7$ is alkyl of one to eight carbon atoms, cycloalkyl of five to seven ring members, cycloalkylalkyl, phenyl or benzyl, and $R_5$ is hydrogen, or a pharmaceutically acceptable acid addition or base salt.

Another preferred embodiment of the present invention in its third generic aspect is a compound of formula 1, wherein $R_1$ is OH; $R_2$ is hydrogen or NHR in which R is hydrogen or $COR_6$ where $R_6$ is methyl; $R_3$ is hydrogen; X is O; $R_4$ is $CH_2OR_7$ in which $R_7$ is alkyl of two to eight carbon atoms, cyclopentyl, cyclohexyl, cyclopentylmethyl, cyclohexylmethyl, phenyl or benzyl, and $R_5$ is hydrogen, or a pharmaceutically acceptable acid addition or base salt.

Particular embodiments of the present invention in its third generic aspect include 2-amino-9[[2-(cyclohexylmethoxy)-1-(hydroxymethyl)ethoxy]methyl]-1,9-dihydro-6H-purine-6-one;
2-amino-9-[[2-(hexyloxy)-1-(hydroxymethyl)ethoxy]methyl]-1,9-dihydro-6H-purin-6-one;
2-amino-9-[[2-heptyloxy)-1-(hydroxymethyl)ethoxy]methyl]-1,9-dihydro-6H-purin-6-one;
2-amino-1,9-dihydro-9-[[1-(hydroxymethyl)-2-(pentyloxy)ethoxy]methyl]-6H-purin-6-one;
2-amino-1,9-dihydro-9-[[1-(hydroxymethyl)-2-(octyloxy)ethoxy]methyl]-6H-purin-6-one; and
2-amino-1,9-dihydro-9-[[1-hydroxymethyl)-2-(phenoxy)ethoxy]methyl]-6H-purin-6-one.

The compounds of formula 1 may be prepared according to the following scheme:

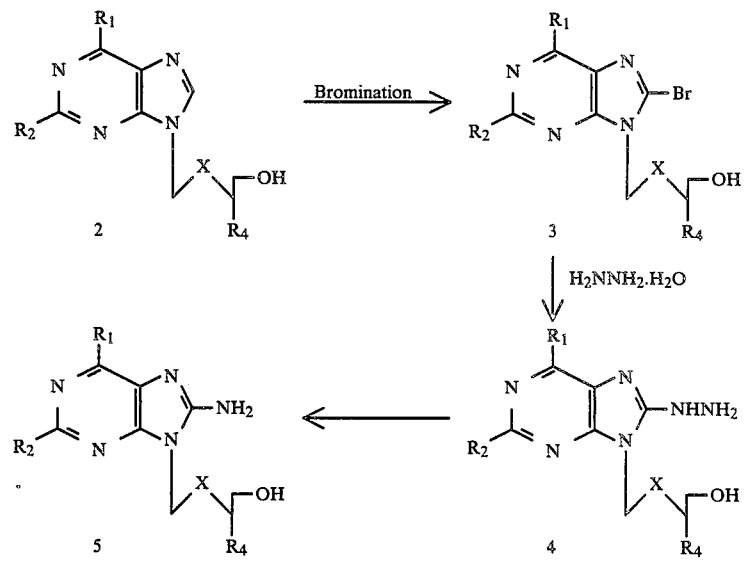

The compounds of formula 2 above where $R_1$=OH, $R_2$=$NH_2$, X=O, $R_4$=H or $CH_2OH$ may be prepared according to British Patent Specification No. 1,567,671 or J. C. Martin, et al, in J Med Chem 26, 759 (1983). The remainder of the compounds of formula 2 above used as starting materials and final products are prepared according to the schemes 1 and 2. Treatment of a compound of formula 2 with N-bromosuccinimide in acetic acid, DMF or methanol produces a compound of formula 3 which when treated with hydrazine hydrate gives the hydrazine of formula 4 or directly the 8-amino derivative of formula 5. The reaction of the 8-bromo compound with hydrazine may or may not proceed entirely to the 8-amino compound. Thus when the 8-hydrazine compound is obtained, it may be further reacted with Raney nickel to allow the reduction to go to completion and afford the desired 8-amino compound. Compounds of formula 5 wherein $R_1$, $R_2$, and $R_4$ have been defined according to compounds of formula 1 may be further converted by known methods to provide $R_5$ substituents of formula 1 or, for example, where $R_1$ is OH, converting said compound to a compound of formula 1 where $R_1$ is SH by known means.

The compounds of the present invention and of the formulae 1, 2, 3, 4, and 5, shown above, may also be prepared by the following schematic sequences of reaction steps as illustrated in Schemes 1 and 2. The numbers in parentheses toward the end of each reaction scheme correspond to the compounds of the present invention as defined above. A more detailed description of the reaction steps is provided in the Examples.

In the preparation of compounds of the present invention and of the formulae 1 and 5, there are employed novel intermediates which are part of the present invention. These are compounds of the formula

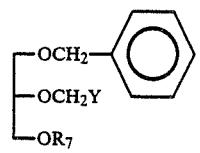

wherein Y is acetyloxy or chloro and $R_7$ is alkyl of one to eight carbon atoms, cycloalkyl of five to seven ring members, cycloalkylalkyl, aryl or arylalkyl. Preferably, $R_7$ is alkyl of two to eight carbon atoms, cyclopentyl, cyclohexyl, cyclopentylmethyl, cyclohexylmethyl, phenyl or benzyl.

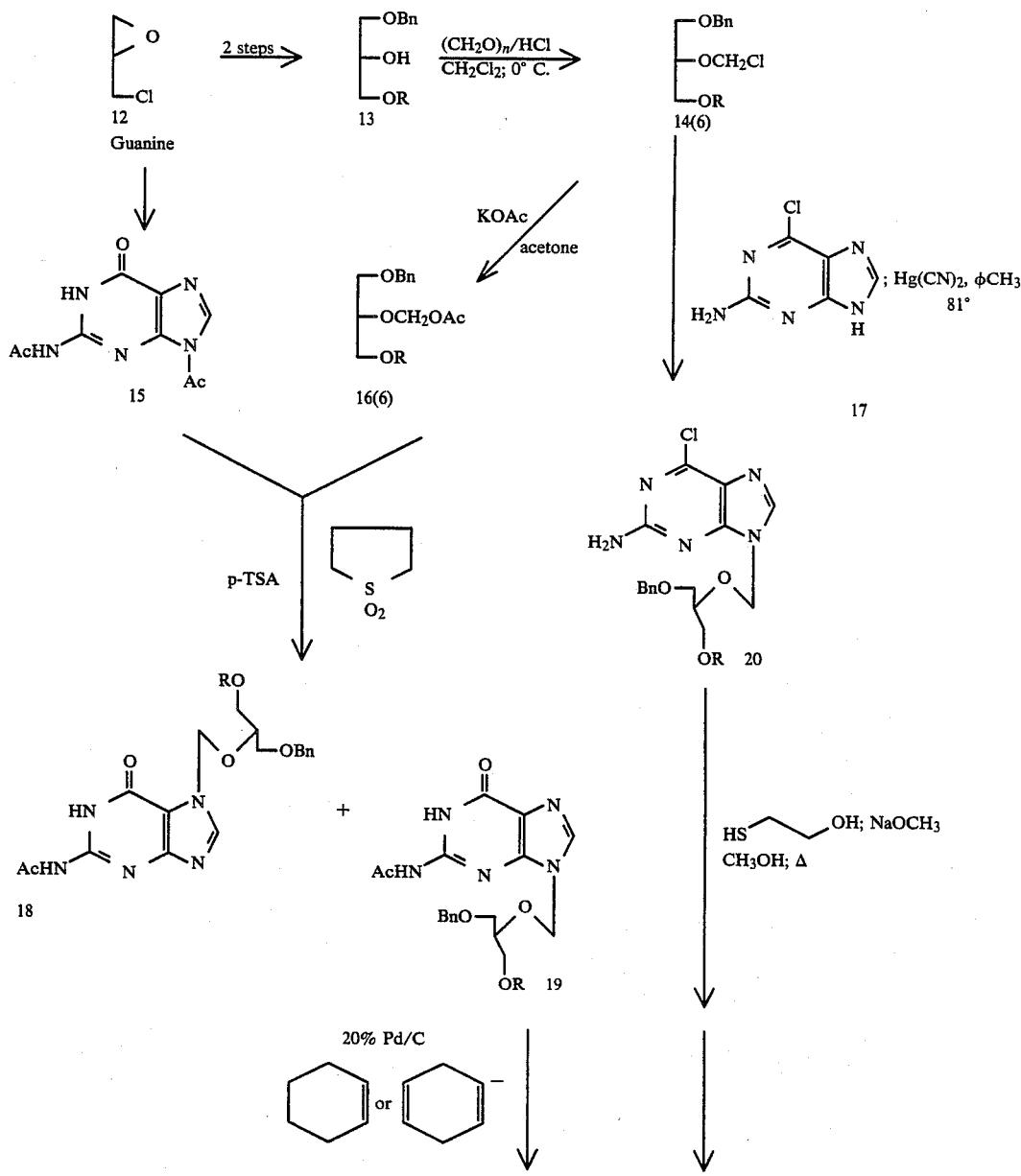

-continued
Scheme 1
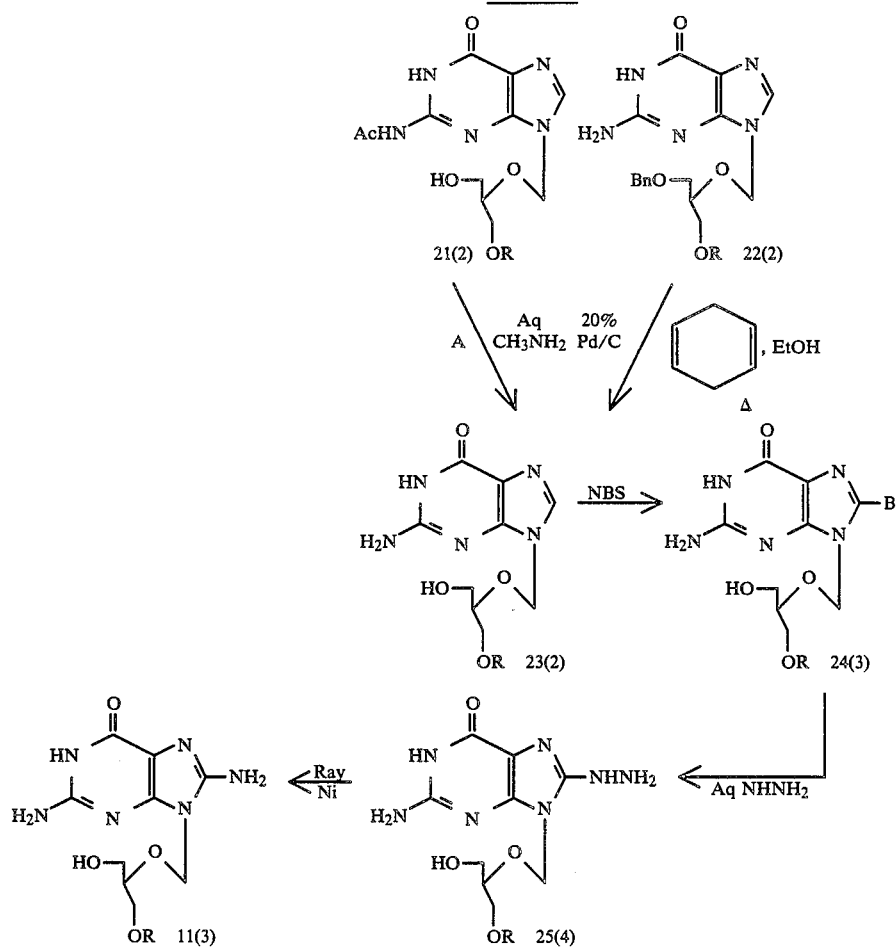
Scheme 2
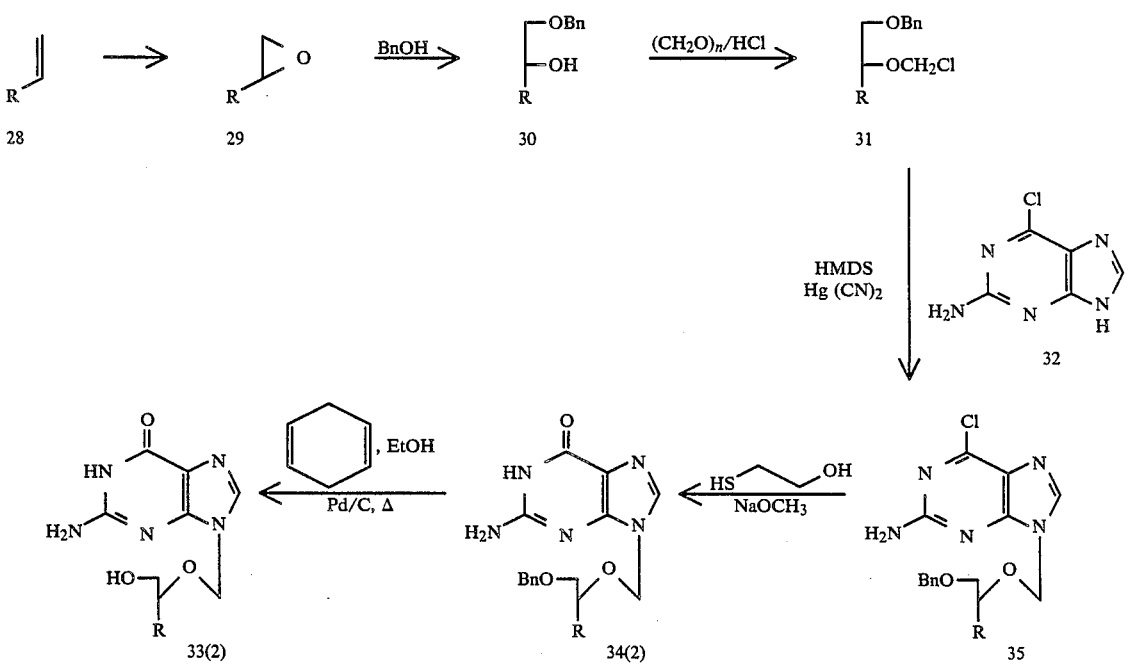

-continued
Scheme 2

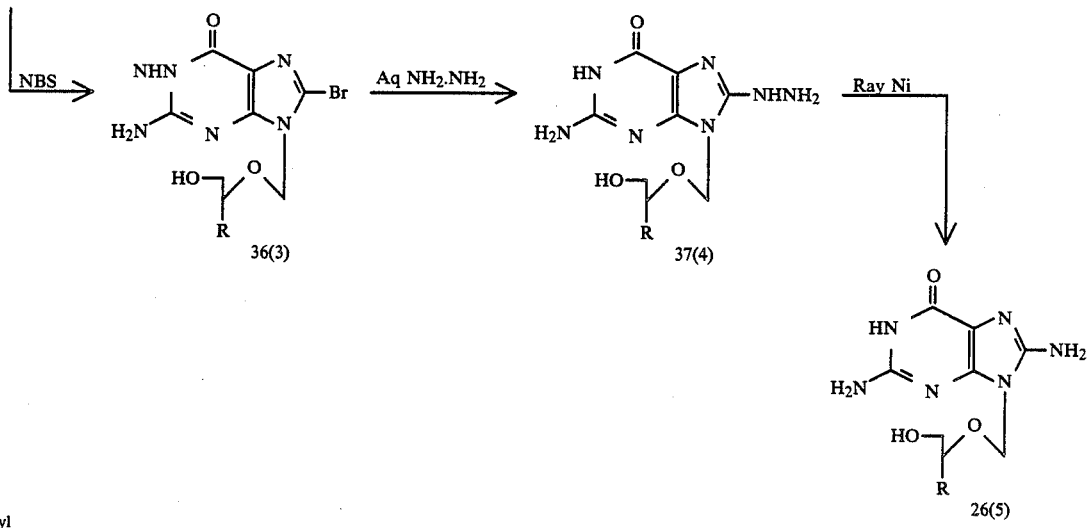

Bn = benzyl

The compounds of the present invention have been shown to exhibit significant enzyme inhibition activity and cytotoxic activity. In the purine nucleoside phosphorylase (PNP-4) enzyme assay, total inhibition was achieved at a concentration less than about 300 micromoles on certain compounds. The same compounds also were found by a standard test (Science, 214, 1137, 1981) to be selectively cytotoxic for T-cells in the presence of 2'-deoxyguanosine at a similar concentration range. For example, 2,8-diamino-9-[(2-hydroxyethoxy)methyl)]-9H-purin-6-ol is selectively cytotoxic to T-cell at a concentration of about 30 micromoles in the presence of 10 micromoles of 2'-deoxyguanosine. Similarly, 2-[(2,8-diamino-6-hydroxy-9H-purin-9-yl)methoxy]-1,3-propanediol is selectively cytotoxic to T-cell at a concentration of about 7 micromoles in the presence of 10 micromoles of 2'-deoxyguanosine. Both compounds were nontoxic to B-cell in the presence of the same amount of 2'-deoxyguanosine. Since T-cells play a central role in immune response, use of the compounds of the invention is contemplated for the immunoregulation of autoimmune diseases such as rheumatoid arthritis, systemic lupus erythematosus, inflammatory bowel disease, cancer, and viral diseases, transplantation, juvenile diabetes, myasthenia gravis, and multiple sclerosis. The present invention thus includes compositions containing a compound of formula 1 in treating disease such as autoimmune disease characterized by abnormal immune response in warmblooded animals. According to this aspect of the invention, the properties of the compounds of the invention are utilized by administering to a warm-blooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well known in the art. For injectionable dosage forms, they are formulated with vehicles such as water, peanut oil, sesame oil, and the like. In these dosage forms, the active ingredient is from about 0.05 grams to 0.5 grams per dosage unit.

The present invention is further illustrated by way of the following examples.

EXAMPLE 1

2-Amino-8-bromo-9-[(2-hydroxyethoxy)methyl]-9H-purin-6-ol[a]

N-bromosuccinimide (0.415 g; 2.3 mmol) is added to a solution of acycloguanosine (0.5 g; 2.2 mmole) (prepared according to British Pat. No. 1,567,671) in acetic acid (7 ml) and the mixture stirred at room temperature for 20 hours. The solution is then diluted with water (20 ml) and the precipitated product is filtered, washed, and triturated with hot water to give 0.25 g of white solid, mp>300° C.

[a] . . . The structure of this compound is disclosed in Biochem. Pharm., 30, 3071–3077 (1981) by P. M. Keller, et. al.

EXAMPLE 1A

The procedure described in Example 1 is repeated to prepare the following 8-bromo-9-substituted guanines starting from appropriate 9-substituted guanines in each case using acetic acid, methanol or DMF as solvent:

2-amino-8-bromo-9-[[2-(heptyloxy)-1-(hydroxymethyl)ethoxy]methyl]-1,9-dihydro-6H-purin-6-one, mp>250° C., dec;

2-amino-8-bromo-9-[[2-(hexyloxy)-1-(hydroxymethyl)ethoxy]methyl]-1,9-dihydro-6H-purin-6-one, mp>250° C., dec;

2-amino-8-bromo-9-[[2-butoxy-1-(hydroxymethyl)ethoxy]methyl]-9H-purin-6-ol, mp>200° C.;

2-amino-8-bromo-1,9-dihydro-9-[[1-(hydroxymethyl)-2-(octyloxy)ethoxy]methyl]-6H-purin-6-one, mp 223°–226° C., dec;

2-amino-8-bromo-9-[[2-(hexyloxy)-1-(hydroxymethyl)ethoxy]methyl]-1,9-dihydro-6H-purin-6-one, mp 212°–214° C.;

2-amino-8-bromo-9[[2-ethoxy-1-(hydroxymethyl)ethoxy]methyl]-1,9-dihydro-6H-purin-6-one, mp 217°–219° C., dec;

2-amino-8-bromo-1,9-dihydro-9-[[1-(hydroxymethyl)-2-(pentyloxy)ethoxy]methyl]-6H-purin-6-one, mp>250° C., dec;

2-amino-8-bromo-9-[[2-(cyclohexylmethoxy)-1-(hydroxymethyl)ethoxy]methyl]-1,9-dihydro-6H-purin-6-one, mp 210°-212° C. (dec);

2-amino-8-bromo-1,9-dihydro-9-[[1-(hydroxymethyl)-2-phenoxyethoxy]methyl]-6H-purin-6-one, mp 218°-219° C., dec;

2-amino-8-bromo-1,9-dihydro-9-[[2-hydroxy)-1-[(4-methoxyphenoxy)methyl]ethoxy]methyl]-6H-purin-6-one; mp 205°-210° C., dec;

2-amino-8-bromo-1,9-dihydro-9-[[1-(hydroxymethyl)-2-(4-methylphenoxy)ethoxy]methyl]-6H-purin-6-one, mp 207°-208° C., dec;

2-amino-8-bromo-1,9-dihydro-9-[[2-(4-chlorophenoxy)-2-(hydroxymethyl)ethoxy]methyl]-6H-purin-6-one; and 2-amino-8-bromo-1,9-dihydro-9-[[[1-(hydroxymethyl)nonyl]oxy]methyl]-6H-purin-6-one, mp 211°-212° C., dec.

EXAMPLE 2

2,8-Diamino-9-[(2-hydroxyethoxy)methyl)]-9H-purin-6-ol

The crude 2-amino-8-bromo-9-[(2-hydroxyethoxy)methyl]-9H-purin-6-ol from acycloguanosine (3.17 g; 0.14 mol) is suspended in water (10 ml) and 97% hydrazine (4 ml) is added to the mixture. The mixture is refluxed for 48 hours, cooled and filtered to give a white solid (1.6 g) which is triturated with hot water (75 ml) to give the analytical sample (1.5 g), mp>300° dec.

EXAMPLE 3

2-[(2-Amino-8-bromo-6-hydroxy-9H-purin-9-yl)methoxy]-1,3-propanediol

N-bromosuccinimide (0.375 g; 2.1 mmol) is added to a solution of 9'-[(1,3-dihydroxy-2-propoxy)methyl]guanine (0.5 g; 1.9 mmole) [prepared according to J. C. Martin; C. A. Dvorak, D. F. Smee, T. R. Matthews, and J. P. H. Verheyden, J Med Chem 26, 759-761 (1983)] in acetic acid (7 ml). The suspension is stirred for 1.5 hours at room temperature and then diluted with water (60 ml). The aqueous solution is concentrated and the residue is recrystallized from water to give 0.44 g of the product; mp>300° dec.

EXAMPLE 4

2-[(2,8-Diamino-6-hydroxy-9H-purin-9-yl)methoxy]-1,3-propanediol

A mixture of 2-[(2-amino-8-bromo-6-hydroxy-9H-purin-9-yl)methoxy]-1,3-propanediol (13.7 g; 41 mmole) and 97% hydrazine (6.07 ml) in water (300 ml) is heated to reflux for 48 hours. At the end of this time, the solution is cooled and filtered to give 9.15 g of crude solid. The crude product is suspended in water (120 ml) and Raney nickel (9 g) is added. The mixture is heated at reflux for 6 hours, filtered hot and cooled. The crystals are collected and dried to give 7.15 g of the product, mp>280° dec.

EXAMPLE 4A

The procedure described in Example 4 is repeated to prepare the following 8-amino-9-substituted guanines starting from appropriate 8-bromo-9-substituted guanines in each case using methoxyethanol as a cosolvent as necessary to make a homogeneous reaction mixture:

2,8-diamino-9-[[2-ethoxy-1-(hydroxymethyl)ethoxy]methyl]-9H-purin-6-ol, mp>220° C., dec;

2,8-diamino-9-[[2-(hexyloxy)-1-(hydroxymethyl)ethoxy]methyl]-1,9-dihydro-6H-purin-6-one, mp>265° C., dec;

2,8-diamino-9-[[2-butoxy-1-(hydroxymethyl)ethoxy]methyl]-9H-purin-6-ol, mp>240° C., dec;

2,8-diamino-1,9-dihydro-9-[[1-(hydroxymethyl)-2-(pentyloxy)ethoxy]methyl]-6H-purin-6-one, mp 274°-277° C., dec;

2,8-diamino-9-[[2-(heptyloxy)-1-(hydroxymethyl)ethoxy]methyl]-1,9-dihydro-6H-purin-6-one, mp>260° C., dec;

2,8-diamino-9-[[2-(hexyloxy)-1-(hydroxymethyl)ethoxy]methyl]-1,9-dihydro-6H-purin-6-one, mp 260°-265° C., dec;

2,8-diamino-9-[[2-(cyclohexylmethoxy)-1-(hydroxymethyl)ethoxy]methyl]-1,9-dihydro-6H-purin-6-one, mp 242°-247° C., dec;

2,8-diamino-1,9-dihydro-9-[[1-(hydroxymethyl)-2-(octyloxy)ethoxy]methyl]-6H-purin-6-one, mp>265° C., (dec);

2,8-diamino-1,9-dihydro-9-[[1-(hydroxymethyl)-2-phenoxyethoxy]methyl]-6H-purin-6-one, mp 265°-271° C., dec;

2,8-diamino-1,9-dihydro-9-[[2-hydroxy-1-[(4-methoxyphenoxy)methyl]ethoxy]methyl]-6H-purin-6-one;

2,8-diamino-1,9-dihydro-9-[[1-hydroxymethyl)-2-(4-methylphenoxy)ethoxy]methyl]-6H-purin-6-one; mp>250° C., dec;

2,8-diamino-1,9-dihydro-9-[[2-(4-chlorophenoxy)-1-hydroxymethyl)ethoxy]methyl]-6H-purin-6-one; and 2,8-diamino-1,9-dihydro-9-[[[1-(hydroxymethyl)nonyl]oxy]methyl]-6H-purin-6-one.

EXAMPLE 5

9-[[2-Benzyloxy-1-(benzyloxymethyl)-ethoxy]methyl]-8-hydrazine-guanine

A mixture of 9-[[2-benzyloxy-1-(benzyl oxymethyl)-ethoxy]methyl]guanine (2.1 g) [prepared according to K. K. Ogilvie, V. O. Cheriyan, B. K. Radatus, K. O. Smith, K. S. Galloway, and W. L. Kennell, Can J Chem, 60, 3005 (1982)] and N-bromosuccinimide (0.94 g) in acetic acid (21 ml) is stirred overnight and then is diluted with water and extracted with chloroform. The chloroform extract is dried and concentrated to give 2.3 g of yellow oil. The crude oil is suspended in ethanol (100 ml) and treated with 95% hydrazine. The solution is heated to reflux for 24 hours. The reaction mixture is then cooled and the product (0.75 g) filtered and dried, mp>210° dec.

EXAMPLE 6

8-Amino-9-[[2-benzyloxy-1-(benzyloxymethyl)-ethoxy]methyl]-guanine

A mixture of 9-[[2-benzyloxy-1-(benzyloxymethyl)ethoxy]methyl]-8-hydrazine-guanine (0.45 g; 0.98 mmol), water (40 ml), ethanol (40 ml), ammonium hydroxide (20 ml) and Raney nickel (1 g) is heated to reflux for 24 hours. The catalyst is filtered off and the filtrate concentrated to a solid which is recrystallized from ethanol to give 0.16 g of analytical sample, mp 255°-260° dec.

EXAMPLE 7

N-[9-[[1-(Butoxymethyl)-2-(phenylmethoxy)ethoxy]methyl]-6-hydroxy-9H-purin-2-yl]acetamide Dry HCl (g) is bubbled into a stirred mixture of paraformaldehyde (1.45 g, 0.048 mol) and 1-butoxy-3-(phenylmethoxy)-2-propanol (5.0 g, 0.021 mol) in methylene chloride (57 ml) at 0° C. until all the solid is dissolved. The resulting solution is stored at 0° C. for 16 hours, dried over MgSO$_4$, and then evaporated to give chloromethyl glycerol ether as a very unstable clear oil. The clear oil is then added dropwise to a stirred mixture of potassium acetate (5.0 g, 0.051 mol) in acetone (60 ml). The mixture is stirred for 16 hours at room temperature and then filtered and evaporated. The residual oil is dissolved in toluene, washed with saturated NaHCO$_3$ and water, dried, and evaporated to give the acetoxy derivative as an oil (5.6 g) which is immediately used for condensation with diacetylguanine.

A mixture of diacetylguanine (4.6 g, 0.0195 mol) and crude acetoxy derivative from above (5.6 g), p-toluene sulfonic acid (43 mg) and sulfolane (5 ml) is heated to 95° C. under nitrogen atmosphere for 72 hours. At 24 hours and 48 hours, additional amounts of p-toluene sulfonic acid (20 mg each) are added. After 72 hours, the mixture is cooled, diluted with toluene and filtered. The filtrate is concentrated, chromatographed, and recrystallized from toluene to provide the desired product (1.33 g), mp 139°–141° C.

EXAMPLE 8

The procedure described in Example 7 is repeated to prepare the following guanine-2-acetamide derivatives, starting from diacetylguanine and appropriate 1-(alkoxy or alkyl or substituted phenoxy)-3-(phenylmethoxy)-2-propanols in each case.

N-[6,9-dihydro-9-[[1-[(octyloxy)methyl]-2-(phenylmethoxy)ethoxy]methyl]-6-oxo-1H-purin-2-yl]acetamide, mp 127°–132° C.;

N-[6,9-dihydro-6-oxo-9-[[1-(phenoxymethyl)-2-(phenylmethoxy)ethoxy]methyl]-1H-purin-2-yl]acetamide, mp 144°–146° C., and N-[9-[[1-(ethoxymethyl)-2-(phenylmethoxy)ethoxy]methyl]-6,9-dihydro-6-oxo-1H-purin-2-yl]acetamide, mp 131°–133° C., dec.

EXAMPLE 9

2-Amino-9-[[2-butoxy-1-(hydroxymethyl)ethoxy]methyl]-9H-purin-6-ol

A mixture of N-[9-[[1-(butoxymethyl)-2-(phenylmethoxy)ethoxy]methyl]-6-hydroxy-9H-purin-2-yl]acetamide (1.15 g, 25.9 mmol), 20% palladium on carbon (0.2 g), cyclohexene (20 ml), and ethanol (10 ml) is heated at reflux under N$_2$. After 8 and 20 hours, additional amounts of catalyst (0.1 g) are added. After 36 hours, the solution is cooled, filtered through celite, and the filter cake is washed with DMF/ethanol. The filtrates are combined, refiltered and concentrated. The residue is mixed with aq. methyl amine (20 ml) and the mixture is heated at reflux for two hours, filtered and concentrated. The residue is recrystallized from water to give the desired product (0.7 g), mp 208°–211° C.

EXAMPLE 10

The procedure described in Example 9 is repeated to prepare the following 9-substituted guanine derivatives, starting from N-[9-substituted-6-hydroxy-9H-purin-2-yl]acetamides in each case. Cyclohexene and cyclohexadiene can either be used in the transfer hydrogenation reaction:

2-amino-9-[[2-ethoxy-1-(hydroxymethyl)ethoxy]methyl]-1,9-dihydro-6H-purin-6-one, mp 206°–209° C.;

2-amino-1,9-dihydro-9[[1-(hydroxymethyl)-2-phenoxyethoxy]methyl]-6H-purin-6-one, mp 195°–198° C.; and 2-amino-1,9-dihydro-9-[[1-(hydroxymethyl)-2-(octyloxy)ethoxy]methyl]-6H-purin-6-one, mp 227°–230° C.

EXAMPLE 11

2-Amino-9-[[1-[(heptyloxy)methyl]-2-[phenylmethoxy]ethoxy]methyl]-1,9-dihydro-6H-purin-6-one A mixture of 2-amino-6-chloropurine (Aldrich Chemical Co.) 11.2 g, 0.066 mol) hexamethyldisilazane (160 ml), and ammonium sulfate (1.09 g) is refluxed for 2.5 hours and then cooled, concentrated and pumped to dryness. The residue is dissolved in dry toluene (210 ml) and is treated with Hg(CN)$_2$. The mixture is heated to 80° C. and a solution of 2-(chloromethoxy)-1-(heptyloxy-3-(phenylmethoxy)propane (prepared from 1-(heptyloxy)-3-(phenylmethoxy)-2-propanol (19 g, 0.068 mol), paraformaldehyde (4 g) and dry HCl (g) in CH$_2$Cl$_2$ (160 ml) as described in the first part of Example 7, in toluene (210 ml) is added to the solution and heated to 80°–85° C. for 2.5 hours. The mixture is cooled, concentrated, and diluted with CH$_2$Cl$_2$ (1.0 L) and is allowed to stand overnight. The CH$_2$Cl$_2$ solution is filtered, washed with 30% KI, 10% potassium carbonate solution and water. The organic layer is dried and concentrated. The residue is chromatographed over silica gel column using a high pressure liquid chromatographic instrument (Waters Prep 500). The column is eluted with ethyl acetate and hexane (1:1) to give the condensation product (i.e., chloropurine derivative) (6.45 g) which is hydrolysed as follows.

A mixture of the above chloropurine derivative (6.42 g, 0.0139 mol) methanol (150 ml) and sodium methoxide (3 g, 0.056 mol) is treated with mercaptoethanol (4.4 ml) and water (0.26 ml). The mixture is then heated to reflux under nitrogen for two hours and then an additional amount of sodium methoxide (1.9 g) is added. The reaction mixture is heated to reflux for an additional 4.0 hours, cooled, and concentrated to about 50 ml. The concentrate is diluted with water (120 ml) and the solution is acidified to pH 6.0. The solid precipitate is filtered, washed with water, and dried. The crude product is then recrystallized from methanol/water to give an analytical sample (4.25 g), mp 185°–187° C.

EXAMPLE 12

The procedure described in Example 11 is repeated to prepare the following 9-substituted guanines starting from 2-amino-6-chloropurine and appropriate 1-(alkoxy or substituted phenoxy or alkyl)-3-(phenylmethoxy)-2-propanols in each case:

2-amino-9-[[1-[(cyclohexylmethoxy)methyl]-2-(phenylmethoxy)ethoxy]methyl]-1,9-dihydro-6H-purin-6-one, mp 198°–201° C.;

2-amino-9-[[1-[(hexyloxy)methyl]-2-(phenylmethoxy)ethoxy]methyl]-1,9-dihydro-6H-purin-6-one; mp 192°–194° C.

2-amino-1,9-dihydro-9-[1-[(pentyloxy)methyl]-2-(phenylmethoxy)ethoxy]methyl]-6H-purin-6-one, mp 192°–194° C.;

2-amino-1,9-dihydro-9-[[-1-[(octyloxy)methyl]-2-(phenylmethoxy)ethoxy]methyl]-6H-purin-6-one, mp 184°–186° C.;
2-amino-1,9-dihydro-9-[[1-(phenoxy)methyl)-2-(phenylmethoxy)ethoxy]methyl]-6H-purin-6-one;
2-amino-1,9-dihydro-9-[[[1-[(phenylmethoxy)methyl]hexyl]oxy]methyl-6H-purin-6-one, mp 206°–208° C.;
2-amino-1,9-dihydro-9[[[1-[(phenylmethoxy)methyl]nonyl]oxy]methyl-6H-purin-6-one, mp 205°–207° C.;
2-amino-9-[[1-[(4-chlorophenoxy)methyl]-2-[phenylmethoxy]ethoxy]methyl]-1,9-dihydro-6H-purin-6one, mp>210° C.;
2-amino-1,9-dihydro-9-[[1-[(4-methoxyphenoxy)methyl]-2-[phenylmethoxy]ethoxy]methyl]-6H-purin-6-one, mp 150°–156° C.; and
2-amino-1,9-dihydro-9-[[1-[(4-methylphenoxy)methyl]-2-[phenylmethoxy]ethoxy]methyl]-6H-purin-6-one, mp 198°–200° C.

EXAMPLE 13

2-Amino-9-[[2-(heptyloxy)-1-(hydroxymethyl)ethoxy]methyl]-1,9-dihydro-6H-purin-6-one A mixture of 2-amino-9-[[1-[(heptyloxy)methyl]-2-(phenylmethoxy)ethoxy]methyl]-1,9-dihydro-6H-purin-6-one (3.9 g, 8.97 mmol), ethanol (200 ml), cyclohexadiene (87 ml, 92.3 mmol), and 20% palladium on charcoal (1.5 g) is heated to reflux under nitrogen atmosphere. After seven hours an additional amount of 20% palladium on charcoal (0.5 g) is added and the mixture is heated to reflux for a total of 18 hours. The mixture is filtered hot and then allowed to cool. The solid formed is collected and dried to give the desired purine (1.95 g), mp 224°–225° C.

EXAMPLE 14

The procedure described in Example 13 is repeated to prepare the following 9-substituted guanines starting from appropriate phenylmethoxy derivatives described in Example 11 and 12.
2-amino-1,9-dihydro-9-[[[1-(hydroxymethyl)hexyl]oxy]methyl]-6H-purine-6-one, mp 228°–229° C.;
2-amino-1,9-dihydro-9-[[[1-(hydroxymethyl)nonyl]oxy]methyl]-6H-purin-6-one, mp >250° C., dec;
2-amino-9-[[2-(ethoxy)-1-(hydroxymethyl)ethoxy]methyl]-1,9-dihydro-6H-purin-6-one, mp 206°–209° C.;
2-amino-9-[[2-(butoxy)-1-(hydroxymethyl)ethoxy]methyl]-9H-purin-6-ol, mp 208°–211° C.;
2-amino-9-[[2-(hexyloxy)-1-(hydroxymethyl)ethoxy]methyl]-1,9-dihydro-6H-purin-6-one;
2-amino-1,9-dihydro-9-[[1-(hydroxymethyl)-2-(penyloxy)ethoxy]methyl]-6H-purin-6-one, mp 218°–220° C.;
2-amino-1,9-dihydro-9-[[1-(hydroxymethyl)-2-(octyloxy)ethoxy]methyl]-6H-purin-6-one, mp 227°–230° C.;
2-amino-9-[[2-(cyclohexylmethoxy)-1-(hydroxymethyl)ethoxy]methyl]-1,9-dihydro-6H-purine-6-one, mp>260° C., dec;
2-amino-1,9-dihydro-9-[[1-(hydroxymethyl)-2-phenoxyethoxy]methyl]-6H-purin-6-one, mp 195°–198° C.;
2-amino-1,9-dihydro-9-[[1-(hydroxymethyl)-2-(4-methylphenoxy)ethoxy]methyl]-6H-purin-6-one, mp 206°–208° C.;
2-amino-1,9-dihydro-9-[[2-(hydroxy-1-[(4-methoxyphenoxy)methyl]ethoxy]methyl]-6H-purine-6-one, mp 210°–217° C., dec; and
2-amino-9-[[2-(4-chlorophenoxy)-1-(hydroxymethyl)ethoxy]methyl]-1,9-dihydro-6H-purin-6-one.

SYNTHESIS OF STARTING MATERIALS

EXAMPLE A

1-Butoxy-3-(phenylmethoxy)-2-propanol n-Butanol (2.5 ml, 27 mmol) is added to a suspension of sodium hydride (50% in mineral oil; 1.3 g, 27 mmol) in DMF (5 ml) and the mixture is then heated to 80° C. for 1.0 hours when all the sodium hydride is consumed. A solution of 2,3-epoxypropyl benzyl ether (benzyl glycidylether*) (4.52 g, 27 mmol) in DMF (5 ml) is added slowly to the n-butoxide solution. The mixture is then heated to 80° C. for 16 hours, diluted with water and extracted with ether. The ether layer is dried and concentrated to give an oil which is distilled to provide the desired product (3.1 g), bp 125°–130°/0.8–0.5 mm.

*Benzyl glycidyl ether is prepared according to the published procedure (J. R Bacon and M. J. Collis, Chem. and Ind., 1971, 930) or purchased from commercial source.

EXAMPLE B

The procedure described in Example A is repeated to prepare the following 1-alkoxy or aryloxy-3-(phenylmethoxy)-2-propanols, starting from appropriate alkanols or phenols in each case.
1-(ethoxy)-3-(phenylmethoxy)-2-propanol, bp 92°–99° C./0.25–0.3 mm;
1-(pentyloxy)-3-(phenylmethoxy)-2-propanol, bp 115°–118° C./0.3 mm;
1-(hexyloxy)-3-(phenylmethoxy)-2-propanol, bp 123°–125° C./0.12 mm;
1-(heptyloxy)-3-(phenylmethoxy)-2-propanol, bp 141° C./0.36 mm; and
1-(octyloxy)-3-(phenylmethoxy)-2-propanol, bp 150°–155° C./0.7 mm.

EXAMPLE C 1-(Phenylmethoxy)-2-decanol

Benzyl alcohol (108 g, 1.0 mol) is added to a suspension of 50% sodium hydride-mineral oil (48 g, 1.0 mol) in DMF (200 ml) at room temperature. The mixture is then heated to 80° C. for two hours. A solution of 1,2-epoxydecane* (85 ml) in DMF (50 ml) is added slowly to the sodium salt over 30 minutes and the mixture is then heated at 80° C. for 20 hours. The reaction mixture is cooled, diluted with water, neutralized with acetic acid, and extracted with ether. The ether extract is concentrated to give an oil which is distilled to give the desired product (131 g), bp 178°–180° C./4 mm.

*Purchased from Aldrich Chemical Co. Other epoxides are either purchases or prepared from olefin or epichlorohydrine as the case may be.

EXAMPLE D

The procedure described in Example C is repeated to prepare the following 1-(phenylmethoxy)alkanols, starting from appropriate 1,2-epoxides in each case.
1-(cyclohexylmethoxy)-3-(phenylmethoxy)-2-propanol, bp 136°–139° C./0.24–0.22 mm;
1-(phenylmethoxy)-2-heptanol, bp 125°–130° C./3–5 mm;
1-(phenoxy)-3-(phenylmethoxy)-2-propanol, bp 148°–157° C./0.32 mm;
1-(4-methylphenoxy)-3-(phenylmethoxy)-2-propanol, bp 194° C./2 mm;
1-(4-methoxyphenoxy)-3-(phenylmethoxy)-2-propanol, bp 175°–184° C./0.4 mm; and
1-(4-chlorophenoxy)-3-(phenylmethoxy)-2-propanol, bp 188°–190° C./1.2–1.3 mm.

We claim:
1. A compound of the formula

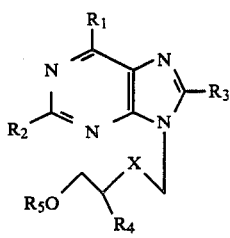

wherein $R_1$ is OH or SH; $R_2$ is hydrogen, NHR in which R is hydrogen or $COR_6$ where $R_6$ is alkyl of one to four carbon atoms, phenyl, phenyl substituted by (i) fluoro, (ii) chloro, (iii) bromo, (iv) trifluoromethyl, (v) alkyl of one to four carbon atoms, (vi) hydroxy, or (vii) alkoxy of one to four carbon atoms, or arylalkyl wherein alkyl is of one to four carbon atoms and aryl is phenyl or phenyl substituted by (i) fluoro, (ii) chloro, (iii) bromo, (iv) alkyl of one to four carbon atoms, (v) trifluoromethyl, (vi) hydroxy, (vii) alkoxy of one to four carbon atoms; $R_3$ is bromine or NHR where R is hydrogen or $COR_6$, wherein $R_6$ is as defined above; X is O or S; $R_4$ is hydrogen or $CH_2OR_5$ in which $R_5$ is hydrogen, alkyl of one to eight carbon atoms, phenyl, phenyl substituted by (i) fluoro, (ii) chloro, (iii) bromo, (iv) trifluoromethyl, (v) alkyl of one to four carbon atoms, (vi) hydroxy, or (vii) alkoxy of one to four carbon atoms, or arylalkyl wherein alkyl is of one to four carbon atoms, and aryl is phenyl or phenyl substituted by (i) fluoro, (ii) chloro, (iii) bromo, (iv) alkyl of one to four carbon atoms, (v) trifluoromethyl, (vi) hydroxy, or (vii) alkoxy of one to four carbon atoms, $COR_6$ or

and $R_6$ is as defined above; with the proviso that when $R_1$ is OH, $R_2$ is $NH_2$, $R_3$ is bromine, and $R_5$ is hydrogen or $COR_6$, then $R_4$ is not a hydrogen or $CH_2OR_5$ wherein $R_5$ is the same $COR_6$ as is defined above or a pharmaceutically acceptable base salt or acid addition salt.

2. A compound of claim 1 wherein $R^3$ is bromine.

3. A compound of claim 1 wherein $R^3$ is NHR.

4. A compound according to claim 3, wherein $R_1$ is OH or SH; $R_2$ is hydrogen or NHR in which R is hydrogen or $COR_6$ wherein $R_6$ is alkyl of one to four carbon atoms or phenyl; $R_3$ is $NH_2$; X is O or S; $R_4$ is hydrogen or $CH_2OR_5$ in which $R_5$ is hydrogen, alkyl of one to eight carbon atoms, phenyl, or benzyl, or a pharmaceutically acceptable base of acid addition salt thereof.

5. A compound according to claim 4, wherein $R_1$ is OH; $R_2$ is hydrogen or $NH_2$; $R_3$ is $NH_2$; X is O; $R_4$ is hydrogen or $CH_2OR_5$ in which $R_5$ is hydrogen.

6. A compound according to claim 2, wherein $R_1$ is OH; $R_2$ is hydrogen or $NH_2$; $R_3$ is bromine; X is O; $R_4$ is hydrogen or $CH_2OR_5$ in which $R_5$ is hydrogen.

7. A compound according to claim 2, wherein $R_1$ is OH or SH; $R_2$ is hydrogen or NHR in which R is hydrogen or $COR_6$ where $R_6$ is alkyl of 1-4 carbon atoms or phenyl; $R_3$ is bromine; X is O or S; $R_4$ is hydrogen or $CH_2OR_5$ in which $R_5$ is hydrogen, alkyl of 1-8 carbon atoms, phenyl, or benzyl, or a pharmaceutically acceptable base or acid addition salt thereof.

8. A compound according to claim 5, and being 2,8-diamino-9-[(2-hydroxyethoxy)methyl]-9H-purin-6-ol.

9. A compound according to claim 5, and being 2-[(2,8-diamino-6-hydroxy-9H-purin-9-yl)methoxy]-1,3-propanediol.

10. A compound according to claim 6, and being 2-[(2-amino-8-bromo-6-hydroxy-9H-purin-9-yl)methoxy]-1,3-propanediol.

11. A compound according to claim 4, and being 2,8-diamino-1,9-dihydro-9-[[1-(hydroxymethyl)-2-phenoxyethoxy]methyl]-6H-purin-6-one.

12. 2-amino-9-[[2-(heptyloxy)-1-(hydroxymethyl)ethoxy]methyl]-1,9-dihydro-6H-purin-6-one.

13. 2-amino-1,9-dihydro-9-[[1-(hydroxymethyl)-2-phenoxyethoxy]methyl]-6H-purin-6-one.

* * * * *